(12) United States Patent
Winheim et al.

(10) Patent No.: US 8,398,665 B2
(45) Date of Patent: Mar. 19, 2013

(54) LANCING SYSTEM FOR WITHDRAWING A BODY FLUID

(75) Inventors: Sven Winheim, Hünenberg (CH); Thomas Sowden Reinhold, Münster (DE); Thomas Seul, Schmalkalden (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 248 days.

(21) Appl. No.: 12/901,773

(22) Filed: Oct. 11, 2010

(65) Prior Publication Data

US 2011/0224712 A1    Sep. 15, 2011

(30) Foreign Application Priority Data

Oct. 15, 2009 (EP) .................................... 09013019

(51) Int. Cl.
*A61B 17/34* (2006.01)
*A61B 5/151* (2006.01)

(52) U.S. Cl. ...................................................... 606/182
(58) Field of Classification Search .......... 606/181–184; 600/583
See application file for complete search history.

(56) References Cited

U.S. PATENT DOCUMENTS

| | | | |
|---|---|---|---|
| 4,442,836 A | 4/1984 | Meinecke et al. | |
| 4,469,110 A | 9/1984 | Slama | |
| 4,924,879 A | 5/1990 | O'Brien | |
| 5,035,704 A | 7/1991 | Lambert et al. | |
| 5,196,025 A | 3/1993 | Ranalletta et al. | |
| 5,938,679 A | 8/1999 | Freeman et al. | |
| 6,080,172 A | 6/2000 | Fujiwara | |
| 6,231,531 B1 | 5/2001 | Lum et al. | |
| 6,749,618 B2 | 6/2004 | Levaughn et al. | |
| 6,858,015 B2 * | 2/2005 | List | 600/583 |

(Continued)

FOREIGN PATENT DOCUMENTS

DE   89 00 203.2   3/1990
EP   0 458 451 A1   11/1991

(Continued)

OTHER PUBLICATIONS

European Application No. 09 01 3019, Search Report, mailed Mar. 23, 2010.

(Continued)

*Primary Examiner* — Elizabeth Houston
(74) *Attorney, Agent, or Firm* — Woodard, Emhardt, Moriarty, McNett & Henry LLP

(57) ABSTRACT

Lancing system for withdrawing body fluid having a lancing element and a lancing instrument, which includes a lancing drive, by which a lancing movement of a lancing element is driven. The lancing drive comprises a drive source and a transmission having a housing coupling mechanism which includes at least two transmission links, a housing bearing, and a coupling element adapted for coupling a lancing element thereto. A lancing depth limiting stop is positioned in the housing so that a stop surface of the lancing element contacts the lancing depth limiting stop during the forward phase of the lancing movement. The housing coupling mechanism comprises a length compensation device to ensure a distance adaptation of the spacing between the lancing element and a housing bearing of the housing coupling mechanism during contact of the stops and further movement of the lancing drive.

7 Claims, 1 Drawing Sheet

U.S. PATENT DOCUMENTS

| | | |
|---|---|---|
| 7,223,276 B2 | 5/2007 | List et al. |
| 8,118,824 B2 | 2/2012 | Roe |
| 8,142,466 B2 * | 3/2012 | Lipoma et al. ............ 606/182 |
| 2003/0028126 A1 | 2/2003 | List |
| 2005/0038465 A1 | 2/2005 | Shraga |
| 2006/0155317 A1 | 7/2006 | List |
| 2008/0082117 A1 | 4/2008 | Ruf |
| 2008/0269639 A1 | 10/2008 | Korner et al. |
| 2010/0069943 A1 | 3/2010 | Roe |
| 2011/0224712 A1 | 9/2011 | Winheim et al. |

FOREIGN PATENT DOCUMENTS

| | | |
|---|---|---|
| EP | 1 254 632 A1 | 11/2002 |

OTHER PUBLICATIONS

U.S. Appl. No. 12/627,420 to Hans List, Office Action mailed Apr. 5, 2012.

* cited by examiner

LANCING SYSTEM FOR WITHDRAWING A BODY FLUID

CROSS-REFERENCE TO RELATED APPLICATION

This application claims the benefit of European Patent Application No. 09 013 019.6, filed Oct. 15, 2009, the entire disclosure of which is hereby incorporated by reference.

BACKGROUND

The invention relates to a lancing system for withdrawing a body fluid from the skin of a human or animal. The body fluid is typically blood. Many applications, however, are concerned with acquiring a sample of interstitial liquid. Hereafter reference is made, without restriction of the generality, to blood as an example, also for other body fluids which can be acquired from the skin.

The system includes a lancing element adapted for single use (disposable) for piercing into the skin, and a lancing instrument having a drive for driving the lancing movement.

Disposable lancing elements are used since many years for withdrawing a small quantity of blood from a body part (usually from a finger or ear lobe) for analytic-diagnostic purposes. In this context, the lancing elements are typically referred to as lancets. Lancets provided for manual piercing are typically used by medically trained personnel. Nevertheless the piercing causes significant pain.

Lancing instruments which contain a lancing drive are also used since many years. The lancing instrument can be implemented as disposable item having a fixedly integrated lancet. More common are instruments which are usable multiple times and have a coupling element, by which one lancet at a time can be replaceably connected to the lancing drive. The instruments and lancets are elements which are adapted to one another and are provided by the same producer. They are therefore designated as a "lancing system" or "blood withdrawal system".

A spring is typically used as the drive source for the lancing drive in the housing of the lancing instrument. However, other drive sources are also used, such as an electric motor or an electromagnetic linear drive. A lancing element guide is provided to ensure that the lancing movement takes place on a predetermined lancing path.

At the beginning of the development, very simple designs of the drive were typical, in which the lancet was fastened directly to one end of a compression spring positioned in an elongated housing (U.S. Pat. No. 4,469,110). In order to control the lancing depth, in such systems, the movement path of the lancet in the lancing direction was limited by a stop surface of the lancet hitting a corresponding lancing depth limiting stop in the housing of the lancing instrument.

In another design, described in U.S. Pat. No. 4,442,836, the movement of the lancet is driven by a first spring in the direction toward the skin surface up to a reversal point (forward phase of the lancing movement), while a second spring is used as the drive source for the retraction movement of the lancet (retraction phase of the lancing movement). The second spring becomes effective after a force coupling between the first spring and the lancet has been interrupted. In order to ensure a defined position of the reversal point of the lancet movement, the force transmission between the drive spring and the lancet is interrupted at a defined point of the movement path.

Blood withdrawal systems of this type do not meet the high requirements which are to be fulfilled if regular monitoring of specific analytic values of the blood is required. This applies in particular for diabetics, who must monitor their blood sugar frequently, in order to keep their blood sugar level continuously within specific target limits, by insulin injections which are adapted to the demand (which varies strongly as a function of the food consumption, physical activity, etc.). It has been proven by extensive scientific studies that a dramatic regression of the most severe long-term damages of diabetes mellitus (for example, retinopathy with resulting blinding of the patient) can be achieved using intensive therapy on the basis of at least four blood analyses per day.

Great progress in this regard has been achieved by a drive type which can be designated as the "housing-coupled drive". Such a drive comprises a transmission, by which a movement of the drive source (such as a spring or electric motor) is converted into a lancing movement of the lancing element, the transmission including a housing coupling mechanism, which comprises at least two transmission links, a housing bearing, and a coupling element for coupling the lancing element thereto. A first housing-side transmission link is connected to the housing of the lancing instrument by means of the housing bearing, and a second lancing-element-side transmission link is connected to the coupling element. The lancing element is connected via the housing coupling mechanism to a part of the housing of the lancing instrument in such a manner that it is moved axially in the direction of the lancing movement and is connected to the housing part and that a specified distance from the housing part is ensured at the reversal point of the lancing movement. Housing-coupled drives are known in various embodiments:

U.S. Pat. No. 4,924,879 discloses a lancing instrument having a rotor which is borne by the housing and driven by a spring, and which is coupled via a connecting rod to the lancing element. The rotor forms the housing-side transmission link and the housing bearing forms its rotational bearing. The lancing-element-side transmission link is formed by the connecting rod, to which a lancing element holder is coupled via a pivot joint, the holder acting as a coupling element for coupling the lancing element thereto.

U.S. Pat. No. 5,318,584 also discloses a lancet drive having a drive rotor on which a drive spring acts on one side (drive side) and which is coupled on the other side via a control curve to the lancet so that the rotation of the drive rotor is converted into the desired lancing movement. In this case, the rotor again forms the housing-side transmission link and the housing bearing forms its rotational bearing. The lancing-element-side transmission link is formed by a control curve rider, which travels along its control curve during the rotation of the drive rotor and is fixedly connected to a lancet holder, which forms the coupling element for coupling the lancet thereto.

Further embodiments of housing-coupled drives having rotors are described in U.S. Pat. No. 7,223,276. The housing-side transmission link is again formed by a drive rotor having a control curve and the lancing-element-side transmission link is formed by a control curve rider, which is fixedly connected to a coupling element for coupling a lancing element thereto. Deviating from the above-mentioned embodiments, the coupling element is in this case not a lancing element holder, in which the lancing element is seated and which is guided in the housing by an axial guide and thus indirectly guides the lancing element. Rather, the lancing element is directly guided in a corresponding hole of the lancing instrument. At its rear end it has a recess which allows the coupling element (in this case a coupling rod head) to be coupled on.

U.S. Pat. No. 6,858,015 describes a design in which the coupling element is connected to the lancing instrument housing by means of levers which are coupled via pivot joints. The coupling element is formed by a lancet holder, which is connected via a pivot joint to a housing-side pivot lever, which forms the lancing-element-side transmission link. The housing-side transmission link is formed by a second pivot lever, which is linked via a further pivot bearing to the housing. The housing bearing is in this case not immovably fastened on the housing, but rather arranged and adapted in such a manner that it is displaceable in the tensioning phase of the lancet drive. However, the design makes sure that the housing bearing is located in a precisely defined position relative to the housing when the lancing movement is executed, in particular when the lancing element is located at the reversal point of the lancing movement. This is decisive for the precision of the lancing depth.

These examples show that the term "transmission" is to be understood here in the general meaning, namely as a kinematic device which is used for coupling and converting movements. The transmission links are the coupling elements of a transmission in this meaning. In the known housing-coupled drives, the housing coupling mechanism provides a precise coupling between the lancing element and the housing, at least at the reversal point of the lancing movement, in such a manner that the reversal point of the lancing movement has a defined specified distance to the housing bearing (which is fixed on the housing at least at the reversal point of the lancing movement).

SUMMARY

A housing-coupled drive provides a very good reproducibility of the lancing movement, which in turn is a precondition for a reproducible lancing depth and thus for a low perception of pain with sufficient blood acquisition. However, this reproducibility is dependent on the quality of the connection between the housing bearing and the coupling element which has to be very exact.

In particular, the rotational bearings, pivot bearings, and curve controllers of the transmission links which produce the connection, must be largely free of play and operate with very little friction. This requires significant expense in manufacturing technology. Simultaneously it must be taken into account that the lancing instruments are to be produced in large numbers at the lowest possible costs.

On this basis, the invention addresses the problem to achieve further optimization of contrary requirements, namely most reasonable production costs and outstanding reproducibility, at the same time.

The object is achieved by a lancing system according to claim 1.

The invention combines design features of two design principles which have heretofore been viewed as contradictory:
- On the one hand, it uses a housing-coupled drive, whose basic principle comprises achieving an exactly defined piercing depth solely by the coupling between the coupling element (and thus the lancing element) and a housing bearing.
- On the other hand, it uses a stop which was typical in earlier instruments having "free flying" lancing elements.

In order to allow the combination of these apparently contradictory development lines, the housing coupling mechanism has a length compensation device, by which a distance adaptation of the spacing between the lancing element and the housing bearing is ensured during contact of the stops and further movement of the lancing drive. This distance adaptation prevents the housing-coupled drive from jamming and thus becoming inoperative, when the two stops hit one another. It was established that an optimum lancing drive may be provided by the invention. On the one hand, the housing coupling mechanism can be manufactured with lower precision and thus more cost-effectively, on the other hand, a precise piercing depth is ensured by the stop.

The invention not only relates to lancing systems which are used only for the purpose of acquiring a blood droplet for subsequent analysis using a separate analysis instrument. Rather, it is also directed to so-called integrated systems, by which not only the blood withdrawal, but also the analysis is performed, preferably without additional handling steps by the user. The lancing element typically has a hollow needle, through which the sample is suctioned.

The present invention is thus directed in general to lancing systems of various types. The lancing element, which is pierced into the skin, can be implemented as a solid needle (as in the described lancets) or as a capillary needle (having an open capillary or in the form of a hollow needle with closed peripheral walls). If reference is made to lancets or other special embodiments, this is for exemplary purposes and without restriction of the generality. The explained facts apply with suitable adaption to other embodiments, as well.

BRIEF DESCRIPTION OF THE DRAWINGS

The invention is explained hereafter on the basis of an exemplary embodiment which is schematically shown in the figures. The described features may be used individually or in combination to provide preferred embodiments of the invention.

DESCRIPTION OF THE SELECTED EMBODIMENTS

Figure 1:
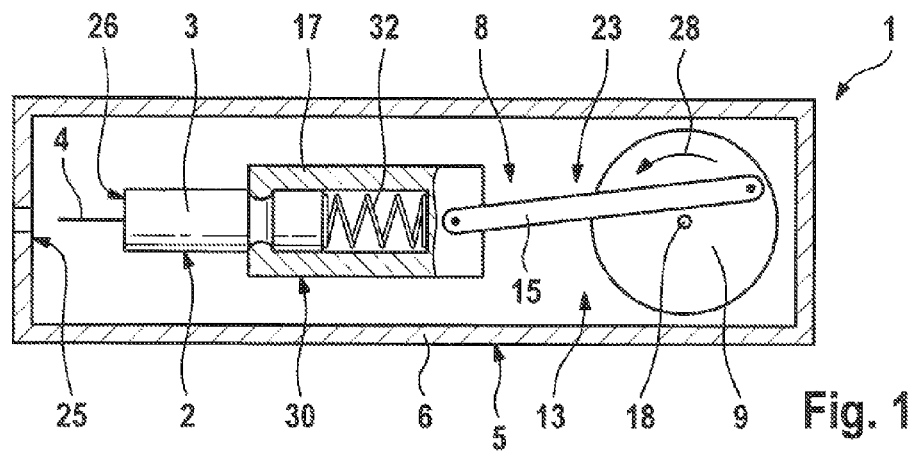
FIGS. 1 to 3 show a schematic side view of a lancing system according to the invention, with the housing in open state, in three different movement phases.

The lancing system 1, which is shown in very schematic form in the figures, includes a lancing element 2 having a lancing element body 3 and a needle 4 as well as a lancing instrument 5 having a housing 6. A lancing drive, which is designated as a whole by 8, is located in the housing 6.

Figure 2:
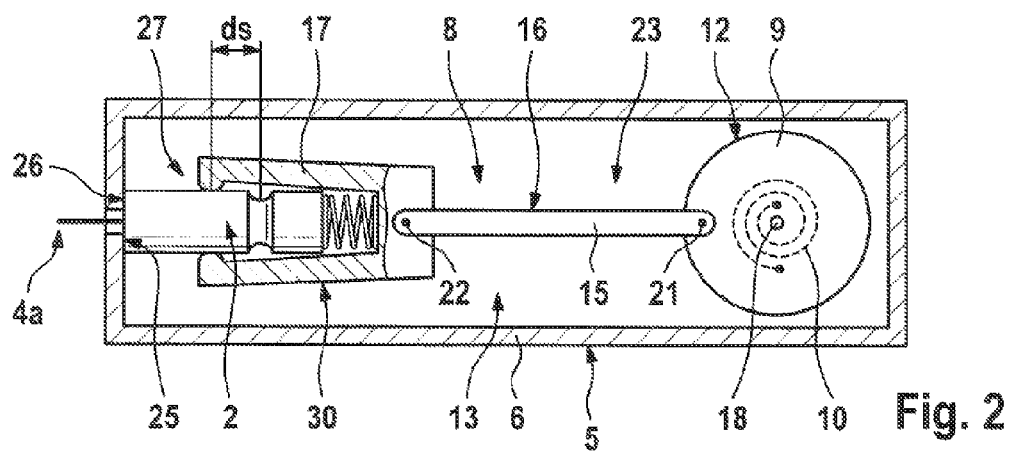

The lancing drive 8 includes a drive rotor 9, which can be rotationally driven by a drive source 10, here a coiled spring, which is concealed by the drive rotor 9 and is therefore shown by dashed lines (for the sake of clarity only in FIG. 2). The drive rotor 9 forms a first, housing-side transmission link 12 of a transmission designated overall by 13. The transmission 13 additionally includes a connecting rod 15 which forms a second, lancing-element-side transmission link 16, and a coupling element 17 for coupling the lancing element 2 to the lancing drive. The housing-side transmission link is connected to the housing by means of a housing bearing 18. Here the housing bearing is formed by the rotation shaft of the drive rotor 9. The second transmission link 16, i.e., the connecting rod 15, is linked via pivot bearings 21, 22 on one side to the drive rotor 9 and on the other side to the coupling element 17.

The transmission links 12, 16, the housing bearing 18, and the coupling element 17 form a housing coupling mechanism 23, by which the lancing element 2 is coupled to the housing during its lancing movement, which is executed on a predetermined piercing path. The lancing drive 8 is accordingly a housing-coupled drive. In contrast to above-mentioned lancing instruments, however, it is not designed in such a manner that, at the reversal point of the lancing movement, the lancing element 2 has a specified spacing from the housing part, on which the housing bearing 18 is located, in such a manner that the reversal point of the lancing movement and the lancing depth are determined by the housing coupling mechanism 23. Rather, a lancing depth limiting stop 25 is position in the housing 6 so that a stop surface 26 correspondingly positioned on the lancing element 2 contacts the lancing depth limiting stop 25 during the forward phase of the lancing movement, so that the movement of the lancing element 2 is limited in the piercing direction by the two stops 25, 26, i.e., by contact of the stop surface 26 with the lancing depth limiting stop 25. In the illustrated preferred embodiment, the stop surface 26 is located on the forward front side (in the piercing direction) of the lancing element 3.

Jamming of the drive is prevented by a length compensation device 27, which ensures a reduction of the spacing between the lancing element 2 and the housing bearing 18 upon contact of the stop surface 26 with the lancing depth limiting stop 25 and further movement of the lancing drive 8. This is explained hereafter on the basis of the movement phases of the lancing drive 8 shown in FIGS. 1 to 3.

FIG. 1 shows the lancing drive in the tensioned state of the rotor 9, before the lancing movement is started by triggering a trigger (not shown). After the triggering, the drive rotor 9 rotates in the direction of the arrow 28 and the rotational movement is converted by the connecting rod 15 into a translational movement of the coupling element 17 and thus the lancing element 2 on a predetermined piercing path, which, as is typical, runs on the longitudinal axis of the lancing instrument 5. The coupling element 17, which is implemented in the illustrated case as the lancet holder 30, is guided by a guide (not shown for the sake of clarity).

The housing coupling mechanism 23 of the lancing drive 8 is dimensioned so that the stop surface 26 of the lancing element 2 hits the lancing depth limiting stop 25 of the housing 6 before the reversal point of the movement of the housing coupling mechanism 23 is reached. Starting at the moment in which the two stops 25, 26 are in contact, the length compensation device 27 performs its function. In the illustrated preferred embodiment, the distance adaptation (i.e., reduction) of the spacing between the lancing element 2 and the housing bearing 18 is achieved by an axial displacement of the lancing element 2 relative to the coupling element 17. The lancing element is essentially held by a friction-type connection. The retention force has to be sufficiently high, however, that the displacement only begins upon contact of the stop surface (26) with the lancing depth limiting stop (25). On the other hand it has to be low enough, that the movement of the lancing drive is not obstructed by the friction to an extent which interferes with its function.

FIG. 2 shows the endpoint of this displacement, which is achieved at maximum longitudinal extension of the housing coupling mechanism 23. The tip 4a of the needle 4 protrudes from the housing 6, so that it penetrates into the skin of a body part placed on the housing opening. The distance adaptation caused by the displacement, i.e., in the illustrated case the total displacement of the lancing element 2 relative to the coupling element 17, is designated by ds. It is shown greatly exaggerated for the sake of clarity. The distance adaptation ds after the contact of the stops up to the reversal point of the lancing movement is preferably at most 0.5 mm, more preferably at most 0.4 mm, and particularly preferably at most 0.3 mm. A spring element 32 is preferably located between the coupling element 17 and the lancing element 2, which counteracts the longitudinal displacement required for the distance adaptation. The precision of the piercing depth setting can thus be further improved thereby.

Figure 3:
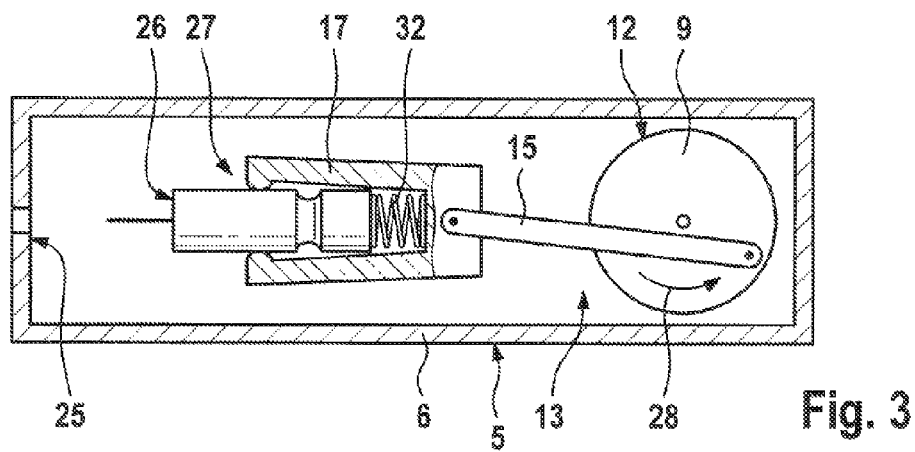

FIG. 3 shows the endpoint of the lancing movement, at which the drive rotor 9 has performed a nearly complete rotation and, via the connecting rod 15, has retracted the coupling element 17 and, with it, the lancing element 2.

Numerous variations of the invention are possible, which may particularly relate to the embodiment of the lancet drive and the distance adaptation. The illustrated drive of the connecting rod type can, for example be replaced by one of the other rotor drives explained supra. The rotational axis of the drive rotor may run in the direction of the lancing movement and also transversely thereto. A pivot lever drive (similarly as described above) can also advantageously be used. The length compensation device can also be provided at a different point of the housing coupling mechanism. In particular, it can be implemented in the area of the housing bearing in such a manner that after the contact of the stops, an axial displacement of the housing bearing relative to the housing is possible. A suitable design is described in U.S. Pat. No. 6,858, 015, which was cited at the beginning (for another purpose, namely in connection with the tensioning procedure).

The invention claimed is:

1. A lancing system for withdrawing body fluid from the skin of a human or animal, the system comprising
   a lancing element having a tip for piercing into the skin, and
   a lancing instrument with a housing, including a lancing drive which drives a lancing movement of a lancing element, which is connected to the lancing drive,
   wherein
   the lancing drive comprises a drive source and a transmission, by which a movement of the drive source is converted into a lancing movement of the lancing element, the lancing movement including a forward phase during which the lancing element is moved along a predetermined piercing path in a piercing direction until the tip of the lancing element penetrates into the skin and a retraction phase during which the lancing element is retracted after reaching a reversal point corresponding to the lancing depth into the skin, and
   the transmission includes a housing coupling mechanism which comprises at least two transmission links, a housing bearing that allows rotation but is translationally fixed relative to the housing, and a coupling element adapted for coupling a lancing element thereto, wherein a first, housing-side transmission link is connected by the housing bearing with housing of the lancing instrument and a second, lancing-element-side transmission link is connected to the coupling element,
   a lancing depth limiting stop is so positioned in the housing that a stop surface of the lancing element contacts the lancing depth limiting stop during the forward phase of the lancing movement, such that the movement of the lancing element in the piercing direction is limited by contact of the stop surface of the lancing element with the lancing depth limiting stop, and
   the housing coupling mechanism has a length compensation device adapted for a distance adaptation of the spacing between the lancing element and the housing bearing, said distance adaptation including a change of the position of the lancing element relative to the coupling element when the stop surface of the lancing element contacts the lancing depth limiting stop and the lancing drive continues to move from a first position to a second position, the tip of the lancing element being closer to the coupling element in the second position than in the first position.

2. The lancing system according to claim 1, characterized in that the length compensation device is provided between the coupling element and the lancing element and is adapted to allow an axial displacement of the lancing element relative to the coupling element after the contact of the stops.

3. The lancing system according to claim 1, characterized in that the coupling element is a lancing element holder, which is borne by an axial guide in the housing.

4. The lancing system according to claim 1, characterized in that a spring element, which acts in the piercing direction on the lancing element, is positioned between the coupling element and the lancing element.

5. The lancing system according to claim 1 characterized in that the connection between the coupling element and the lancing element is a friction-type connection.

6. The lancing system according to claim 1, characterized in that the lancing depth limiting stop is positioned relative to the stop surface of the lancing element so that the distance adaptation (ds) after the contact of the stops up to the reversal point of the lancing movement is at most 0.5 mm, preferably at most 0.4 mm, and particularly preferably at most 0.3 mm.

7. The lancing system according to claim 1, characterized in that the lancing element has a metal needle and a lancing element body made of plastic, and the stop surface is located on a forward front side of the lancing element body in the piercing direction.

* * * * *